United States Patent
Bermudes (12)

(10) Patent No.: US 9,597,379 B1
(45) Date of Patent: Mar. 21, 2017

(54) PROTEASE INHIBITOR COMBINATION WITH THERAPEUTIC PROTEINS INCLUDING ANTIBODIES

(76) Inventor: David Gordon Bermudes, Kenwood, CA (US)

( * ) Notice: Subject to any disclaimer, the term of this patent is extended or adjusted under 35 U.S.C. 154(b) by 1299 days.

(21) Appl. No.: 13/024,179

(22) Filed: Feb. 9, 2011

Related U.S. Application Data

(60) Provisional application No. 61/302,763, filed on Feb. 9, 2010.

(51) Int. Cl.
*A61K 38/55* (2006.01)

(52) U.S. Cl.
CPC .................................. *A61K 38/55* (2013.01)

(58) Field of Classification Search
CPC ..................................................... A61K 38/55
See application file for complete search history.

(56) References Cited

U.S. PATENT DOCUMENTS

2008/0286290 A1* 11/2008 Furusako et al. .......... 424/178.1

OTHER PUBLICATIONS

Laskowski, M., et al. 1980 Ann Rev Biochem 49: 593-626.*

* cited by examiner

*Primary Examiner* — Marsha Tsay
(74) *Attorney, Agent, or Firm* — Steven M. Hoffberg, Esq.; Ostrolenk Faber LLP

(57) ABSTRACT

Protease inhibitors together with protease sensitive therapeutics or diagnostics are provided, which may be ionically or covalently bound, or unbound. The protease inhibitors and/or protease sensitive moiety may be provided in monomeric, homopolymeric, heteropolymeric (for each of the protease and agent) and/or block copolymeric (combining polymers of agent and inhibitor) form. The inhibitors may be native active or e.g., protease activated. Multiple protease inhibitor peptides may be used in-frame with multiple protease cleavage signals (polymeric protease activated protease inhibitors). Combination with the protease inhibitors with the protease sensitive therapeutic enhances the intact, active molecule local-regional or targeted cell or tissue concentration, peak concentration and/or duration of the therapeutic exposure, thereby increasing its therapeutic efficacy. The protease inhibitors are particularly useful for tumor-targeted therapies and for vaccines.

12 Claims, 1 Drawing Sheet

PROTEASE INHIBITOR COMBINATION WITH THERAPEUTIC PROTEINS INCLUDING ANTIBODIES

1. FIELD OF THE INVENTION

This invention is related to the field of therapeutic delivery systems, and methods for improving the delivery, stability and efficacy of protein therapeutics.

2. BACKGROUND OF THE INVENTION

Citation or identification of any reference herein, or any section of this application shall not be construed as an admission that such reference is available as prior art to the present application. The disclosures of each of these publications in their entireties are hereby incorporated by reference in their entirety in this application, and shall be treated as if the entirety thereof forms a part of this application.

Once a rarely used subset of medical treatments, protein therapeutics have increased dramatically in number and frequency of use since the introduction of the first recombinant protein therapeutic, human insulin, 25 years ago. Protein therapeutics already have a significant role in almost every field of medicine, but this role is still only in its infancy. (Leader et al., 2008, Protein therapeutics: a summary and pharmacological classification Nature Reviews Drug Discovery 7, 21-39).

Targeted monoclonal antibodies comprise a major form of therapeutic proteins. Targeting monoclonal antibodies to the tumor can result in the destruction of the tumor cells by antibody-dependent cellular cytotoxicity or complement-dependent cytotoxicity. Similarly, targeting cytokines or immunomodulatory molecules either by bispecific scFv or antibody—ligand fusion proteins to the tumor modulates the immune response against the tumor. In addition, antibody-ligand fusion proteins can induce apoptosis to targeted cells as well as bystander cells by, for example, presenting FasL. A more direct approach to kill the targeted cell is the conjugation of cytotoxic drugs, toxins or radionucleotides to the monoclonal antibodies. The antibody-directed enzyme prodrug therapy (ADEPT) approach specifically aims at causing bystander effects by targeting enzymes to the tumor cell and delivering a prodrug that is converted to a chemotherapeutic by the targeted enzyme. (Schrama et al., 2006, Antibody targeted drugs as cancer therapeutics, *Nature Reviews Drug Discovery* 5, 147-159). Examples of monoclonal antibody therapeutics are shown in Table I. However, means to enhance their protease stability have not been provided, particularly for tumor-targeted antibodies.

TABLE I

Monoclonal antibody therapeutics approved for clinical use. From: An, 2008, Antibody Therapeutics—a mini review. Trends in Bio/Pharmaceutical Industry 2: 24-29.

| Generic Name Trade Name Manufacturer | Launch Date | Therapy Area | Major Indication | Target | Protein Form/Isotype | Delivery | Reference |
|---|---|---|---|---|---|---|---|
| Muromonab Orthoclone/OKT3 Johnson & Johnson | 1986 | AIID | Transplant rejection | CD3 | Murine IgG2a | IV | (16) |
| Abciximab ReoPro Eli Lilly | 1995 | CV | Cardiovascular disease | CD41 | Chimeric Fab | IV | (8) |
| Rituximab Rituxan/MabThera Genentech/Roche | 1997 | Oncology | Non-Hodgkin's Lymphoma | CD20 | Chimeric IgG1 | IV | (17) |
| Daclizumab Zenapax Roche | 1997 | AIID | Transplant rejection | CD25 | Humanized IgG1 | IV | (9) |
| Basiliximab Simulect Novartis | 1998 | AIID | Transplant rejection | CD25 | Chimeric IgG1 | IV | (18) |
| Infliximab Remicade Centocor | 1998 | AIID | Rheumatoid arthritis | TNF alpha | Chimeric IgG1 | IV | (19) |
| Palivizumab Synagis MedImmune | 1998 | ID | Respiratory syncytial virus | RSV F-protein | Chimeric IgG1 | IM | (20) |
| Trastuzumab Herceptin Genentech | 1998 | Oncology | Breast cancer | Hcr2 | Humanized IgG1 | IV | (21) |
| Gemtuzumab/ozogamicin Mylotarg Wyeth | 2000 | Oncology | Acute myclogenous leukemia | CD33 | Humanized IgG4 conjugated with ozogamicin | IV | (22) |
| Alemtuzumab Campath Bayer-Schering | 2001 | Oncology | Chronic lymphocytic leukemia | CD52 | Humanized IgG1 | IV | (23) |
| Ibritumomab tiuxetan Zevalin Biogen/Idec | 2002 | Oncology | Non-Hodgkin's Lymphoma | CD20 | Murine IgG1 conjugated with Yttrium 90 | IV | (24) |
| Omalizumab Xolair Genentech/Novartis | 2003 | Respiratory | Asthma | IgE | Humanized IgG1 | SC | (25) |
| Efalizumab Raptiva Genentech | 2003 | AIID | Psoriasis | CD11A | Humanized IgG1 | SC | (26) |

TABLE I-continued

Monoclonal antibody therapeutics approved for clinical use. From: An, 2008,
Antibody Therapeutics—a mini review. Trends in Bio/Pharmaceutical Industry 2: 24-29.

| Generic Name Trade Name Manufacturer | Launch Date | Therapy Area | Major Indication | Target | Protein Form/Isotype | Delivery | Reference |
|---|---|---|---|---|---|---|---|
| Tositumomab Bexxar GSK | 2003 | Oncology | Non-Hodgkin's Lymphoma | CD20 | Murine IgG2a conjugated with Iodine-131 | IV | (27) |
| Adalimumab Humira Abbott | 2003 | AIID | Rheumatoid arthritis | TNF alpha | Human IgG1 | SC | (11) |
| Cetuximab Erbitux ImClone/BMS | 2003 | Oncology | Colorectal cancer | EGFR | Chimeric IgG1 | IV | (28) |
| I-131 ch-TNT Shanghai Medipharm Biotech Co. | 2003 | Oncology | Advanced lung cancer | Intracellular DNA in tumors | Chimeric IgG1 conjugated with I-131 | IV | (29) |
| Bevacizumab Avastin Genentech | 2004 | Oncology | Colorectal and non-small cell lung cancer | VEGF | Humanized IgG1 | IV | (30) |
| Natalizumab Tysabri Biogen IDEC/Elan | 2004 | CNS/AIID | Multiple sclerosis | VLA4 | humanized IgG1 | IV | (31) |
| Tocilizumab Actemra Roche/Chugai | 2005 | AIID | Castleman's disease | IL-6R | Humanized IgG1 | IV | (32) |
| Ranibizumab Lucentis Genentech/Novartis | 2006 | Ophthalmology | Wet age-related macular degeneration | VEGF | Humanized mab fragment of Avastin | Injection into the eye | (3) |
| Panitumumab Vectibix Amgen | 2006 | Oncology | Colorectal cancer | EGFR | Human IgG2 | IV | (33) |
| Certolizumab pegol Cimzia UCB-Schwarz | 2007 | AIID | Rheumatoid arthritis | TNF alpha | PEGylated Fragment | SC | (4) |
| Eculizumab Soliris Alexion | 2007 | Hematology | PNH (chronic hemolysis) | C5a | Humanized IgG2/IgG4 hybrid | IV | (34) |

3. SUMMARY OF THE INVENTION

Protease inhibitors together with protease sensitive therapeutics are provided. Therefore, the localized in vivo activity of protease-sensitive drugs will be increased. Likewise, the physical region of activity for a highly protease sensitive peptide agent will be generally limited to the region in which both the protease inhibitor and peptide are present at sufficient concentrations.

The polymeric protease activated protease inhibitors can be homo- or hetero-inhibitor polymers, and/or homo- or hetero-protease cleavage site polymers. Combination with the protease inhibitors with the protease sensitive therapeutic enhances the intact, active molecule local-regional or targeted cell or tissue concentration, peak concentration and/or duration of the therapeutic exposure, thereby increasing its therapeutic efficacy. The protease inhibitors are particularly useful for tumor-targeted therapies and for vaccines.

The present invention comprises systems, compositions, and methods for using protease inhibitors together with protease sensitive therapeutics. The protease inhibitors may be ionically bound the protease sensitive therapeutic, covalently bound (e.g., connected through a covalent bond), or unbound. The protease inhibitors include monomeric protease inhibitors, and polymeric inhibitors where the inhibitors are themselves protease activated, or the protease inhibitors may be activated or activated in some other way. The protease cleavage site may be for the same protease that the peptide inactivates, and thus, the protease activates its own inhibitor. The protease inhibitor may be of a competitive or non-competitive type. The protease cleavage site may also be for a protease other than for the protease inhibitor, thus deactivating another protease. Multiple protease inhibitor peptides may be used in-frame with multiple protease cleavage signals (polymeric protease activated protease inhibitors). The polymeric protease activated protease inhibitors can be homo- or hetero-inhibitor polymers, and/or homo- or hetero-protease cleavage site polymers.

Combination of a protease inhibitor with a protease sensitive therapeutic may enhance the intact, active molecule local-regional or targeted cell or tissue concentration, peak concentration and/or duration of the therapeutic exposure, thereby increasing its therapeutic efficacy.

The protease inhibitors are particularly useful for tumor-targeted therapies, which for example include the protease sensitive therapeutic.

The compositions comprising a protease inhibitor and protease-sensitive agent may be administered in traditional manner through oral, transcutaneous, transmucosal, intravenous, intramuscular, intraperitoneal, intrathecal manner, or in situ administration in a solid or liquid form, encapsulated in a polymer or liposome, or employing known administration technologies. On the other hand, the protease inhibitor and/or protease sensitive agent may be produced by a genetically engineered cell or colony of cells, such as prokaryotic cells, e.g., *Salmonella, E. coli*, or *mycoplasma* sp., or eukaryotic cells, such as autologous human cells in the case of a human therapy or diagnostic aid.

4. BRIEF DESCRIPTION OF THE DRAWINGS

5. DETAILED DESCRIPTION OF THE INVENTION

Figure 1:
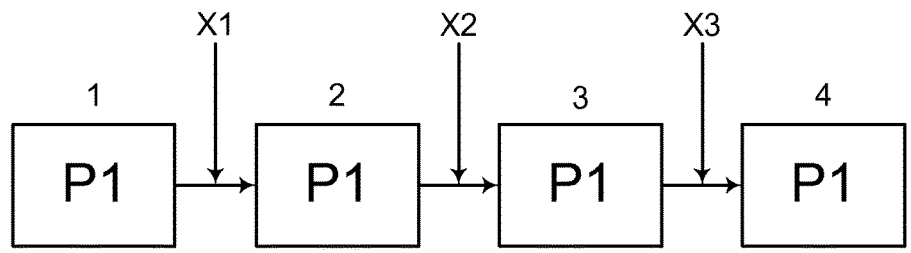
FIG. 1 shows a polymeric protease-activated protease inhibitor.

The present invention provides, according to various embodiments, improved protein therapeutics with increased circulation (enhanced pharmacokinetics), longer half-lives and decreased degradation. In a preferred embodiment, the protein therapeutic is an antitumor antibody.

5.1. Protease Sensitivity

Therapeutic proteins are typically inherently sensitive to extracellular proteases. Proteases may be classified by several different systems, for example, into six groups: serine proteases, threonine proteases, cysteine proteases, aspartate proteases, metalloproteases and glutamic acid proteases. Alternatively, proteases may be classified by the optimal pH in which they are active: acid proteases, neutral proteases, and basic proteases (or alkaline proteases). Many proteases are over-expressed within tumors (Edwards et al. (eds) 2008, The Cancer Degradome: Proteases and Cancer Biology, Springer, 926 pp.) including tissue plasminogen activator, activated protein C, factor Xa, granzyme (A, B, M), cathepsins (e.g., cathepsin B and S), thrombin, plasmin, urokinase, matrix metalloproteaes (types 1-26) membrane matrix metalloproteases (types 1-4), prostate specific antigens (PSA; kallikrein 3-related peptidase), kallikrein 2, elastin, trypsin, chymotrypsin.

A variety of protease assays are known to those skilled in the art. Many protease assays are commercially available, such as the QuantiCleave Fluorescent Protease Assay Kit, and QuantiCleave Protease Assay Kit II (Thermo/Fisher, Rockford, Ill.), Protease Assay Kit (G Biosciences, Maryland Heights, Mo.), PepTag Protease Assay (Promega, Madison, Wis.; 1993 Promega Notes Magazine 44: 2), Viral Protease Assay Kits (AnaSpec, Fremont, Calif.), Protease Assay Kit from Calbiochem (Calbiochem, San Diego, Calif.).

Standard laboratory techniques to measure protease activity, and thus the reduced activity of protease inhibitors, include densitometric, spectrophotometric, colorometric and fluorometric assays, sodium dodecyl sulfate (SDS) polyacrylamide gel electrophoresis (PAGE), two dimentional SDS-PAGE, high pressure liquid chromatography (HPLC) and mass spectroscopy (mass-spec). Examples of protases and their cleavage signals are shown in Table 2.

Protease cleavage sites are defined in the Merops database (Rawlings et al., 2010, MEROPS: The Peptidase Database, Nucleic Acids Res. 2010 (Database issue):D227-33. It will be understood to those skilled in the arts that many proteases do not have strict sequence recognition sites, but rather have sequence preferences and/or frequencies. The MEROPS site depicts the preferences with a weighted pictogram and a table which lists frequencies of occurrence within a cleavage sequence. The table a non-limiting list proteases of tumors, the MEROPS sequence specification, and a simplified representative of an amino acid one letter code recognition sequence (where X is any amino acid) and the cleavage signal is given by a downward arrow) is presented in Table 2.

TABLE 2

Examples of protease cleavage sequences.

| Protease | MEROPS Sequence Designation | Simplified Representative Sequence Designation |
|---|---|---|
| Factor Xa | ia/e/Gfp/R⁺sti/vfs/—/g | (IEGR↓SV) SEQ ID NO: 30 |
| Furin | R/—/Kr/R⁺s/—/—/— | (RXKR↓SX) SEQ ID NO: 31 |
| Plasminogen activator | —/—/—/R⁺R/iv/N/— | (XXR↓RIN) SEQ ID NO: 32 |
| Urokinase | —/sg/Gs/Rk⁺—/r/—/— | (XSGR↓XR) SEQ ID NO: 33 |
| MMP1 | —/pa/—/g⁺li/—/—/— | (GPXG↓LXG) SEQ ID NO: 34 |
| MMP8 | g/Pas/—/g⁺l/—/g/— | (GPQG↓LRG) SEQ ID NO: 35 |
| MMP 13 | g/P/—/g⁺l/—/ga/— | (GPPG↓LXG) SEQ ID NO: 36 |
| Membrane matrix metalloprotease 1 | —/p/—/—⁺l/—/—/— | (LPAG↓LVLX) SEQ ID NO: 37 |
| PSA | si/sq/—/yq⁺s/s/—/— | (SSQY↓SSN) SEQ ID NO: 38 |
| Kallikrein 2 | g/—/—/R⁺—/—/—/gs | (GGLR↓SGGG) SEQ ID NO: 39 |
| Granzyme A | t/—/—/RK⁺sa/—/—/— | (TXXPR↓SX) SEQ ID NO: 40 |
| Granzyme B | v/—/—/D⁺—/—/—/— | (VEXD↓SX) SEQ ID NO: 41 |
| Granzyme M | Ka/vaye/Pa/LM⁺—/—/—/— | (KVPL↓X) SEQ ID NO: 42 |
| Cathepsin B | —/—/l/r⁺—/—/g/— | (XLR↓XXGG) SEQ ID NO: 43 |
| Cathepsin S | —/—/flv/r⁺—/—/—/— | (SGFR↓SXG) SEQ ID NO: 44 |
| Thrombin | —/—/pla/R⁺sag/—/—/— | (AGPR↓SLX) SEQ ID NO: 45 |
| Plasmin | —/—/—/KR⁺—/—/—/— | (AXLK↓SX) SEQ ID NO: 46 |
| Plasminogen | /—/—/KR⁺—/—/—/— | (AXLK↓SX) SEQ ID NO: 47 |

The MEROPS database can be used to identify which proteases to inhibit, by analysis of a particular effector protein and the cleavage sites it contains. Comparison with the target tissue, eg Edwards et al. (eds) 2008, The Cancer Degradome: Proteases and Cancer Biology, Springer, 926 pp is also used to inform the choice. Alternatively, 2-dimentional gel electrophoresis and protein sequencing of radiolabled peptides incubated with the target tumor can be used to identify which aminoacids are being cleaved in a therapeutic protein, and therefore which protease inhibitors to use.

5.2 Protease Inhibitors

Protease inhibitors usable in accordance herewith are preferably based on known polypeptide inhibitors. The inhibitors include both synthetic peptides and naturally occurring, endogenous peptides. Classes of protease inhibitors include: cysteine protease inhibitors, serine protease inhibitors (serpins), trypsin inhibitors, Kunitz STI protease inhibitor, threonine protease inhibitors, aspartic protease inhibitors, metalloprotease inhibitors. Protease inhibitors can also be classified by mechanism of action as suicide inhibitors, transition state inhibitors, protein protease inhibitor (see serpins) and chelating agents. The protease inhibitors are typically protein or polypeptide inhibitors that are activated by protease cleavage, resulting in a time-released "depot" effect.

The C-terminal sequences may provide a free protease inhibitor. The cleavage site may be for the same protease that the peptide inactivates. Thus, the protease activates its own inhibitor. The protease cleavage site may also be for a protease other than for the protease inhibitor, thus deactivating another protease. Multiple protease inhibitor peptides may be used in-frame with multiple protease cleavage signals (polymeric protease activated protease inhibitors), where the inhibitors alternate with cleavage sites. The polymeric protease activated protease inhibitors can be homo- or hetero-inhibitor polymers (i.e., have inhibitors for the same or different proteases, respectively), and/or homo- or hetero-protease cleavage polymers (i.e., have the same or different protease cleavage sites). Examples of proteases upregulated within tumors include: tissue plasminogen activator, activated protein C, factor Xa, granzyme (A, B, M), cathepsin, thrombin, plasmin, urokinase, matrix metaloproteaes, prostate specific antigen (PSA) and kallikrein 2 (e.g., Edwards et al. (eds) 2008, The Cancer Degradome: Proteases and Cancer Biology, Springer, 926 pp.), as well as proteases of lysosomes and the gut.

Protease inhibitors have been reviewed by Laskowski and Kato, 1980, (Annual Review of Biochemistry 49: 593-626), expressly incorporated by reference herein. Serine proteases inhibitors, the largest group, include 1) bovine pancreatic trypsin inhibitor (Kunitz) family, 2) pancreatic secretory trypsin inhibitor (Kazal) family, 3) *Streptomyces* subtilisin inhibitor family, 4) soybean trypsin inhibitor (Kunitz) family, 5) soybean proteinase inhibitor (Bowman-Birk) family 6) potato I inhibitor family, 7) potato II inhibitor family, 8) *Ascaris* trypsin inhibitor family, and 9) others. Protease inhibitors have also been grouped within the MEROPS peptidase database (Rawlings et al., 2008 Nucleic Acids Res. 36 Database issue, D320-325).

Specific examples of protease inhibitors that may be expressed as complete proteins or peptide fragments corresponding to the active inhibitory site include but are not limited to aprotinin, cathepsin inhibitor peptide sc-3130, Niserria protease inhibitor, lympocyte protease inhibitor, maspin, matrix metalloprotease inhibitors, macroglobulins, antithrombin, equistatin, Bowman-Birk inhbitor family, ovomucoid, ovoinhibitor-proteinase inhibitors from avian serum, dog submandibular inhibitors, inter-a-trypsin inhibitors from mammalian serum, chelonianin from turtle egg white, soybean trypsin inhibitor (Kunitz), secretory trypsin inhibitors (Kazal) $a_i$-proteinase inhibitor, *Streptomyces* subtilisin inhibitor, plasminostreptin, plasmin inhibitor, factor Xa inhibitor, coelenterate protease inhibitors, protease inhibitor anticoagulants, ixolaris, human Serpins (SerpinA1 (alpha 1-antitrypsin), SerpinA2, SerpinA3, SerpinA4, SerpinA5, SerpinA6, SerpinA7, SerpinA8, SerpinA9, SerpinA10, SerpinA11, SerpinA12, SerpinA13, SerpinB1, SerpinB2, SerpinB3, SerpinB4, SerpinB5, SerpinB6, SerpinB7, SerpinB8, SerpinC1 (antithrombin), SerpinD1, SerpinE1, SerpinE2, SerpinF1, SerpinF2, SerpinG1, SerpinNI1, SerpinNI2), cowpea trypsin inhibitor, onion trypsin inhibitor, alpha 1-antitrypsin, *Ascaris* trypsin and pepsin inhibitors, lipocalins, CI inhibiotor, plasminogen-activator inhibitor, collegenase inhibitor, Acp62F from *Drosophila*, bombina trypsin inhibitor, *bombyx* subtilisin inhibitor, von Willebrand factor, leukocyte secretory protease inhibitor. Short peptide inhibitors of protease are preferred. Many protease inhibitors have one or more disulfide bonds. Fusion to thioredoxin (trxA) is known to improve protease inhibitor activity (e.g., Furuki et al., 2007, Fukuoka University Science Reports 37: 37-44). Fusion to glutathione-S transferase (GST) and co-expression with disulfide bond isomerase (DsbA) or nusA (Harrison 2000, Expression of soluble heterologous proteins via fusion with NusA protein. *inNovations* 11: 4-7) are also known to improve solubility. Examples of the peptide sequences of short peptide inhibitors is shown in Table 3.

TABLE 3

Sequences of short peptide protease inhibitors

| Protease Inhibitor | Protease(s) inhibited | Protein/Peptide Name and/or Peptide Sequence |
|---|---|---|
| Leupeptin | calpain, plasmin, trypsin, papain, and cathepsin B | Leupeptin |
| Aprotinin | Trypsin Plasmin Tissue kallikrein | RPDFC LEPPY TGPCK ARIIR YFYNA KAGLC QTFVY GGCRA KRNNF KSAED CMRTC GGA SEQ ID NO: 001 |
| Aprotinin homologues | Variable | Brinkmann et al, 1991 Eur J. Biochem 202: 95-99 |
| Protease Inhibitor 15 | Trypsin | Synthetic peptide: CFPGVTSNYLYWFK SEQ ID NO: 002, corresponding to amino acids 245-258 of human protease inhibitor. |
| Tissue protease inhibitor | Serine protease inhibitor, Kazal type 1, mature | DSLGREAKCYNELNGCTKIYDPVCGTDGNTYPNECVLCF ENRKRQTSILIQKSGPC SEQ ID NO: 003 |
| Furin inhibitors | Furin | PAAATVTKKVAKSPKKAKAAKPKKAAKSAAKAVKPK SEQ ID NO: 004 TKKVAKRPRAKRAA SEQ ID NO: 005 TKKVAKRPRAKRDL SEQ ID NO: 006 GKRPRAKRA SEQ ID NO: 007 CKRPRAKRDL SEQ ID NO: 008 CVAKRPRAKRDL SEQ ID NO: 009 CKKVAKRPRAKRDL SEQ ID NO: 010 RRRRRR L6R (hexa-L-arginine) SEQ ID NO: 011 |
| Kallikrein Inhibitors | Kallikrein 2 | SRFKVWWAAG SEQ ID NO: 012 AARRPFPAPS SEQ ID NO: 013 PARRPFPVTA SEQ ID NO: 014 |
| Pepsinogen 1-16 | Pepsin | LVKVPLVRKKSLRQNL SEQ ID NO: 015 Dunn et al., 1983 Biochem J 209: 355-362 |
| Pepsinogen 1-12 | Pepsin | LVKVPLVRKKSL SEQ ID NO: 016 Dunn et al., 1983 Biochem J 209: 355-362 |

TABLE 3-continued

Sequences of short peptide protease inhibitors

| Protease Inhibitor | Protease(s) inhibited | Protein/Peptide Name and/or Peptide Sequence |
|---|---|---|
| Pepsinogen 1-12 4-7 substitution | Pepsin | LVKGGLVRKKSL (II) [Gly4,5] SEQ ID NO: 017<br>LVKVPGGRKKSL (III) [Gly6,7] SEQ ID NO: 018<br>LVKGGGGRKKSL (IV) [Gly4-7] SEQ ID NO: 019<br>Dunn et al., 1983 Biochem J 209: 355-362 |
| Sunflower trysin inhibitor SFTI-1 | Trypsin | GRCTKSIPPICFPD SEQ ID NO: 020 |
| Odorrana trypsin inhibitor | Trypsin | AVNIPFKVHFRCKAAFC SEQ ID NO: 021 |
| Ascaris chymotrypsin elastase inhibitor | Chymtrypsin Elastase | GQESCGPNEV WTECTGCEMK CGPDENTPCP LMCRRPSCEC SPGRGMRRTN DGKCIPASQCP SEQ ID NO: 022 |
| Ascaris trypsin inhibitor | Trypsin | EAEKCBZZPG WTKGGCETCG CAQKIVPCTR ETKPNPQCPR KQCCIASAGF VRDAQGNCIK FEDCPK SEQ ID NO: 023 |
| Ascaris trypsin inhibitor | Trypsin | EAEKCTKPNE QWTKCGGCEG TCAQKIVPCT RECKPPRCEC IASAGFVRDA QGNCIKFEDC PK SEQ ID NO: 024 |
| Onion trypsin inhibitor | Trypsin | MKAALVIFLL IAMLGVLAAE AYPNLRQVVV TGDEEEGGCC DSCGSCDRRA PDLARCECRD VVTSCGPGCK RCEEADLDLN PPRYVCKDMS FHSCQTRCSI L SEQ ID NO: 025 |
| Barley chymotrypsin inhibitor 2 | Chymotrypsin | MSSMEKKPEGVNIGAGDRQNQKTEWPELVGKSVEEAKK VILQDK PAAQIIVLPVGTIVTMEYRIDRVRLFVDRLDNIAQVPRVG SEQ ID NO: 026 |
| Thrombin inhibitors | Thrombin | IQPR SEQ ID NO: 027<br>GSAVPR SEQ ID NO: 028<br>Feng et al., (WO 2004/076484) PEPTIDE INHIBITORS OF THROMBIN AS POTENT ANTICOAGULANTS) |
| Proteosome inhibitors Chymostatin Clasto-tactastatin | Proteosome subunit 3 'chymotryptic-like' (beta5), 'tryptic-like' (beta2) and 'peptidyl-glutamyl peptide hydrolyzing' (beta1). | |
| Urokinase, thrombin, plasmin and trypsin inhibitors | Urokinase, thrombin, plasmin and trypsin | Markowska et al., 2008, Effect of tripeptides on the amindolytic activities of urokinase, thrombin, plasmin and trypsin. Int. J. Peptide Research and Therapeutics 14: 215-218. |

5.3 Therapeutic Proteins

Leader et al., 2008 (Nature Reviews Drug Discovery 7: 21-39, incorporated by reference in its entirety) divided protein therapeutics in to functional categories:
Group I: protein therapeutics with enzymatic or regulatory activity
  Ia: Replacing a protein that is deficient or abnormal.
  Ib: Augmenting an existing pathway.
  Ic: Providing a novel function or activity.
Group II: protein therapeutics with special targeting activity
  IIa: Interfering with a molecule or organism.
  IIb: Delivering other compounds or proteins.
Group III: protein vaccines
  IIIa: Protecting against a deleterious foreign agent.
  IIIb: Treating an autoimmune disease.
  IIIc: Treating cancer.
Group IV: protein diagnostics.

Although other protein therapeutics previously dominated and have had well-established production protocols (e.g., Smales, C M and James, D. C (eds) 2005, Therapeutic Proteins: Methods and Protocols, Human Press), antibody therapeutics have been the most actively developed over the past 10 years. Antibody production is well known to those skilled in the arts (e.g., Dimitrov, A. S. 2009, Therapeutic antibodies: Methods and protocols, Humana Press; Dubel, S, (ed) 2010 Handbook of therapeutic antibodies: technologies, emerging developments and approved therapeutics, Wiley-Blackwell).

5.4 Co-Administration

The protease inhibitors may be mixtures with the therapeutics, and be ionically coupled, or uncoupled to the therapeutic. Methods of preparing such mixtures are known to those skilled in the arts (Singh, M., (ed) 2007, Vaccine adjuvants and delivery systems, Wiley.

5.5 Bioconjugated Protease Inhibitors

In a preferred embodiment, the inhibitor is covalently coupled to the therapeutic. Methods of covalently linking to therapeutic proteins are known to those skilled in the arts (e.g., Bioconjugate techniques, 2nd Ed. Greg T Hermanson Academic Press, Amsterdam, 2008; Bioconjugation Protocols; Strategies and Methods. Christof M. Niemeyer, (ed), Methods in Molecular Biology 283.Humana Press, Totowa, N.J., 2010;

5.6 Genetic Fusions

In the production of therapeutic proteins, genetic constructs can be used to generate fusion proteins. The fusion proteins are generally produced as N-terminal or C-terminal fusions by the addition of DNA, in-frame, that codes for the fusion peptide. For example, the genes encoding monoclonal antibodies can be genetically engineered to be produced as peptide fusions, where the peptides are protease inhibitor peptides. The protease inhibitor peptides can be monomeric or polymeric, and may be activated through cleavage by the protease they inhibit or by other proteases. Methods of generating antibody protein fusions are well known to those skilled in the arts (e.g., Chamow, S. M and Ashkenazi, A. (eds) Antibody Fusion Proteins Wiley-Liss, New York; Kontermann, R. and Dubel, S. Antibody Engineering, Second Edition, 2010, Springer Verlag, Berlin; kreitman and Pastan, Making).

6. EXAMPLES

6.1. Example 1

A Cancer Therapeutic Antibody Coupled to a Polymeric Protease Activated Protease Inhibitor FIG. 1 shows a polymeric protease activated protease inhibitor. Multiple protease inhibitor peptides may be used in-frame with multiple protease cleavage signals (polymeric protease activated protease inhibitors), where the inhibitors alternate with cleavage sites. The polymeric protease activated protease inhibitors can be homo- or hetero-inhibitor polymers (i.e., have multiple inhibitors for the same or different proteases, respectively), and/or homo- or hetero-protease cleavage polymers (i.e., have multiple of the same or different protease cleavage sites). Thus, protease inhibitors 1, 2 and 3 can be the same protease inhibitor or different protease inhibitors, and the protease cleavage sites (downward arrows) can be the same protease cleavage side or different protease cleavage sites.

The protease inhibitors are those known inhibitors for proteases overexpressed in tumors, such as those from Table 2. A therapeutic antibody, such as Herceptin, is coupled to a polymeric protease-activated protease inhibitor. The polymeric protease inhibitor, such as a furin-activated furin inhibitor, in frame with the Herceptin antibody with the amino acid sequence (furin inhbitor IN CAPS; furin cleavage in lower case)

Figure 2:
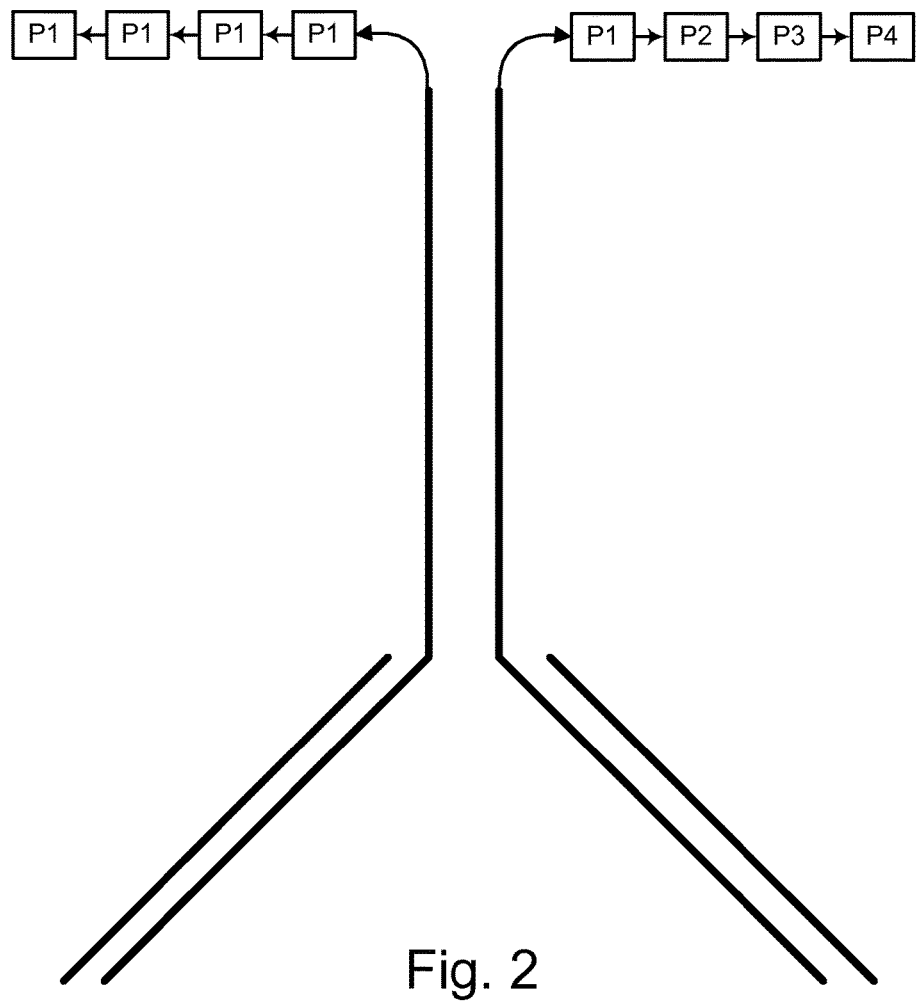
FIG. 2 shows chimeric antibody coupled to polymeric protease-activated protease inhibitors.

```
                                           SEQ ID NO: 029
TKKVAKRPRAKRAArxkr↓sxTKKVAKRPRAKRAArxkr↓sxTKKVAKRP
RAKRAA,
``` is genetically fused or covalently bound using methods known to those skilled in the arts (e.g., Bioconjugate techniques, 2nd Ed. Greg T Hermanson Academic Press, Amsterdam, 2008; Bioconjugation Protocols; Strategies and Methods. Christof M. Niemeyer, (ed), Methods in Molecular Biology 283.Humana Press, Totowa, N.J., 2010; Chamow, S. M and Ashkenazi, A. (eds) Antibody Fusion Proteins Wiley-Liss, New York; Kontermann, R. and Dubel, S. Antibody Engineering, Second Edition, 2010, Springer Verlag, Berlin) to result in an antibody with a polymeric protease inhibitor as shown (FIG. 2). The purified conjugate is then used for the treatment of cancer by injection of an effective amount. Animal models (Teicher, B. (ed) Tumor models in Cancer Research, Humana Press, 2002) may be used to guide human clinical evaluation where dose escalation is used, often beginning with low doses calculated from animal studies.

FIG. 2 shows an antibody (IgG type) conjugated with a polymeric protease activated protease inhibitor. On the left, a homopolymer of protease inhibitor is shown. On the right, a heteropolymer of protease inhibitor is shown. The antibody may be monoclonal or polyclonal, and may act as a targeting therapeutic, catalytic antibody, or diagnostic agent.

What is claimed is:

1. A protease activated polymer comprising a therapeutic agent linked through a protease cleavage site to a plurality of polypeptide protease inhibitors in sequence, the sequence comprising respective polypeptide protease inhibitor monomers linked through respective protease cleavage sites.

2. The protease activated polymer according to claim 1, further comprising a plurality of identical monomeric polypeptide protease inhibitor, wherein the protease activated polymer is purified.

3. The protease activated polymer according to claim 2, further comprising protease cleavage sites for the same protease that the plurality of identical momomeric polypeptide protease inhibitors inhibit.

4. The protease activated polymer according to claim 2, further comprising protease cleavage sites for a different protease than the plurality of identical momomeric polypeptide protease inhibitors inhibit.

5. The protease activated polymer according to claim 1, further comprising a plurality of different monomeric polypeptide protease inhibitors, wherein the protease activated polymer is purified.

6. The protease activated polymer according to claim 5, further comprising protease cleavage sites for the same proteases that the plurality of different momomeric polypeptide protease inhibitors inhibit.

7. The protease activated polymer according to claim 5, further comprising protease cleavage sites for at least one different protease than the plurality of different momomeric polypeptide protease inhibitors inhibit.

8. The protease activated polymer according to claim 5, wherein the plurality of different monomeric polypeptide protease inhibitors are configured to inhibit a plurality of different classes of proteases.

9. The protease activated polymer according to claim 1, wherein the plurality of monomeric polypeptide protease inhibitors in sequence comprise inhibitors of more than one type of protease, the protease activated polymer having protease cleavage sites between monomeric polypeptide protease inhibitors of more than one type, wherein for each type of protease cleavage site a respective monomeric polypeptide protease inhibitor is provided.

10. The protease activated polymer according to claim 1, further comprising a covalently linked therapeutic or diagnostic protein, having at least one protease cleavage site subject to degradation by at least one protease inhibited by at least one of the plurality of momomeric polypeptide protease inhibitors, wherein the protease activated polymer is substantially purified.

11. The protease activated polymer according to claim 1, further comprising a covalently linked enzyme, having at least one protease cleavage site subject to degradation by at least one protease inhibited by at least one of the plurality of monomeric polypeptide protease inhibitors, wherein the protease activated polymer is substantially purified.

12. The protease activated polymer according to claim 1, further comprising a covalently linked antibody, having at least one protease cleavage site subject to degradation by at least one protease inhibited by at least one of the plurality of monomeric polypeptide protease inhibitors, wherein the protease activated polymer is substantially purified.

* * * * *

SEQUENCE LISTING

```
<160> NUMBER OF SEQ ID NOS: 47

<210> SEQ ID NO 1
<211> LENGTH: 58
<212> TYPE: PRT
<213> ORGANISM: Artificial Sequence
<220> FEATURE:
<223> OTHER INFORMATION: Aprotinin

<400> SEQUENCE: 1

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55
```

<210> SEQ ID NO 2
<211> LENGTH: 14
<212> TYPE: PRT
<213> ORGANISM: Artificial Sequence
<220> FEATURE:
<223> OTHER INFORMATION: Protease Inhibitor 15 (amino acids 245-258 of
      human protease inhibitor)

<400> SEQUENCE: 2

Cys Phe Pro Gly Val Thr Ser Asn Tyr Leu Tyr Trp Phe Lys
1               5                   10

<210> SEQ ID NO 3
<211> LENGTH: 56
<212> TYPE: PRT
<213> ORGANISM: Artificial Sequence
<220> FEATURE:
<223> OTHER INFORMATION: Tissue Protease Inhibitor

<400> SEQUENCE: 3

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
        35                  40                  45

Leu Ile Gln Lys Ser Gly Pro Cys
    50                  55

<210> SEQ ID NO 4
<211> LENGTH: 36
<212> TYPE: PRT
<213> ORGANISM: Artificial Sequence
<220> FEATURE:
<223> OTHER INFORMATION: Furin Inhibitor

<400> SEQUENCE: 4

Pro Ala Ala Ala Thr Val Thr Lys Lys Val Ala Lys Ser Pro Lys Lys
1               5                   10                  15

Ala Lys Ala Ala Lys Pro Lys Lys Ala Ala Lys Ser Ala Ala Lys Ala
            20                  25                  30

Val Lys Pro Lys
            35

<210> SEQ ID NO 5
<211> LENGTH: 14
<212> TYPE: PRT
<213> ORGANISM: Artificial Sequence
<220> FEATURE:
<223> OTHER INFORMATION: Furin Inhibitor

<400> SEQUENCE: 5

Thr Lys Lys Val Ala Lys Arg Pro Arg Ala Lys Arg Ala Ala
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Furin Inhibitor

<400> SEQUENCE: 6

-continued

```
Thr Lys Lys Val Ala Lys Arg Pro Arg Ala Lys Arg Asp Leu
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Furin Inhibitor

<400> SEQUENCE: 7

Gly Lys Arg Pro Arg Ala Lys Arg Ala
1               5

<210> SEQ ID NO 8
<211> LENGTH: 10
<212> TYPE: PRT
<213> ORGANISM: Artificial Sequence
<220> FEATURE:
<223> OTHER INFORMATION: Furin Inhibitor

<400> SEQUENCE: 8

Cys Lys Arg Pro Arg Ala Lys Arg Asp Leu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Furin Inhibitor

<400> SEQUENCE: 9

Cys Val Ala Lys Arg Pro Arg Ala Lys Arg Asp Leu
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Furin Inhibitor

<400> SEQUENCE: 10

Cys Lys Lys Val Ala Lys Arg Pro Arg Ala Lys Arg Asp Leu
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Furin Inhibitor L6R (hexa-L-arginine)

<400> SEQUENCE: 11

Arg Arg Arg Arg Arg Arg
1               5

<210> SEQ ID NO 12
<211> LENGTH: 10
<212> TYPE: PRT
<213> ORGANISM: Artificial Sequence
<220> FEATURE:
<223> OTHER INFORMATION: Kallikrein Inhibitor

<400> SEQUENCE: 12

Ser Arg Phe Lys Val Trp Trp Ala Ala Gly
```

<210> SEQ ID NO 13
<211> LENGTH: 10
<212> TYPE: PRT
<213> ORGANISM: Artificial Sequence
<220> FEATURE:
<223> OTHER INFORMATION: Kallikrein Inhibitor

<400> SEQUENCE: 13

Ala Ala Arg Arg Pro Phe Pro Ala Pro Ser
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Kallikrein Inhibitor

<400> SEQUENCE: 14

Pro Ala Arg Arg Pro Phe Pro Val Thr Ala
1               5                   10

<210> SEQ ID NO 15
<211> LENGTH: 16
<212> TYPE: PRT
<213> ORGANISM: Artificial Sequence
<220> FEATURE:
<223> OTHER INFORMATION: Pepsinogen 1-16

<400> SEQUENCE: 15

Leu Val Lys Val Pro Leu Val Arg Lys Lys Ser Leu Arg Gln Asn Leu
1               5                   10                  15

<210> SEQ ID NO 16
<211> LENGTH: 12
<212> TYPE: PRT
<213> ORGANISM: Artificial Sequence
<220> FEATURE:
<223> OTHER INFORMATION: Pepsinogen 1-12

<400> SEQUENCE: 16

Leu Val Lys Val Pro Leu Val Arg Lys Lys Ser Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Pepsinogen 1-12 4-7 substitution (II) [Gly4,5]

<400> SEQUENCE: 17

Leu Val Lys Gly Gly Leu Val Arg Lys Lys Ser Leu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Pepsinogen 1-12 4-7 substitution (III) [Gly6,7]

<400> SEQUENCE: 18

Leu Val Lys Val Pro Gly Gly Arg Lys Lys Ser Leu
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Pepsinogen 1-12 4-7 substitution (IV) [GIy4-7]

<400> SEQUENCE: 19

Leu Val Lys Gly Gly Gly Gly Arg Lys Lys Ser Leu
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Sunflower trysin inhibitor SFTI-1

<400> SEQUENCE: 20

Gly Arg Cys Thr Lys Ser Ile Pro Pro Ile Cys Phe Pro Asp
1               5                   10

<210> SEQ ID NO 21
<211> LENGTH: 17
<212> TYPE: PRT
<213> ORGANISM: Artificial Sequence
<220> FEATURE:
<223> OTHER INFORMATION: Odorrana trypsin inhibitor

<400> SEQUENCE: 21

Ala Val Asn Ile Pro Phe Lys Val His Phe Arg Cys Lys Ala Ala Phe
1               5                   10                  15

Cys

<210> SEQ ID NO 22
<211> LENGTH: 61
<212> TYPE: PRT
<213> ORGANISM: Artificial Sequence
<220> FEATURE:
<223> OTHER INFORMATION: Ascaris chymotrypsin elastase inhibitor

<400> SEQUENCE: 22

Gly Gln Glu Ser Cys Gly Pro Asn Glu Val Trp Thr Glu Cys Thr Gly
1               5                   10                  15

Cys Glu Met Lys Cys Gly Pro Asp Glu Asn Thr Pro Cys Pro Leu Met
                20                  25                  30

Cys Arg Arg Pro Ser Cys Glu Cys Ser Pro Gly Arg Gly Met Arg Arg
            35                  40                  45

Thr Asn Asp Gly Lys Cys Ile Pro Ala Ser Gln Cys Pro
        50                  55                  60

<210> SEQ ID NO 23
<211> LENGTH: 66
<212> TYPE: PRT
<213> ORGANISM: Artificial Sequence
<220> FEATURE:
<223> OTHER INFORMATION: Ascaris trypsin inhibitor

<400> SEQUENCE: 23

Glu Ala Glu Lys Cys Asx Glx Glx Pro Gly Trp Thr Lys Gly Gly Cys
1               5                   10                  15

Glu Thr Cys Gly Cys Ala Gln Lys Ile Val Pro Cys Thr Arg Glu Thr
                20                  25                  30

```
Lys Pro Asn Pro Gln Cys Pro Arg Lys Gln Cys Cys Ile Ala Ser Ala
            35                  40                  45

Gly Phe Val Arg Asp Ala Gln Gly Asn Cys Ile Lys Phe Glu Asp Cys
        50                  55                  60

Pro Lys
65

<210> SEQ ID NO 24
<211> LENGTH: 62
<212> TYPE: PRT
<213> ORGANISM: Artificial Sequence
<220> FEATURE:
<223> OTHER INFORMATION: Ascaris trypsin inhibitor

<400> SEQUENCE: 24

Glu Ala Glu Lys Cys Thr Lys Pro Asn Glu Gln Trp Thr Lys Cys Gly
1               5                   10                  15

Gly Cys Glu Gly Thr Cys Ala Gln Lys Ile Val Pro Cys Thr Arg Glu
            20                  25                  30

Cys Lys Pro Pro Arg Cys Glu Cys Ile Ala Ser Ala Gly Phe Val Arg
        35                  40                  45

Asp Ala Gln Gly Asn Cys Ile Lys Phe Glu Asp Cys Pro Lys
    50                  55                  60

<210> SEQ ID NO 25
<211> LENGTH: 101
<212> TYPE: PRT
<213> ORGANISM: Artificial Sequence
<220> FEATURE:
<223> OTHER INFORMATION: Onion trypsin inhibitor

<400> SEQUENCE: 25

Met Lys Ala Ala Leu Val Ile Phe Leu Leu Ile Ala Met Leu Gly Val
1               5                   10                  15

Leu Ala Ala Glu Ala Tyr Pro Asn Leu Arg Gln Val Val Val Thr Gly
            20                  25                  30

Asp Glu Glu Glu Gly Gly Cys Cys Asp Ser Cys Gly Ser Cys Asp Arg
        35                  40                  45

Arg Ala Pro Asp Leu Ala Arg Cys Glu Cys Arg Asp Val Val Thr Ser
    50                  55                  60

Cys Gly Pro Gly Cys Lys Arg Cys Glu Glu Ala Asp Leu Asp Leu Asn
65                  70                  75                  80

Pro Pro Arg Tyr Val Cys Lys Asp Met Ser Phe His Ser Cys Gln Thr
                85                  90                  95

Arg Cys Ser Ile Leu
            100

<210> SEQ ID NO 26
<211> LENGTH: 84
<212> TYPE: PRT
<213> ORGANISM: Artificial Sequence
<220> FEATURE:
<223> OTHER INFORMATION: Barley chymotrypsin inhibitor 2

<400> SEQUENCE: 26

Met Ser Ser Met Glu Lys Lys Pro Glu Gly Val Asn Ile Gly Ala Gly
1               5                   10                  15

Asp Arg Gln Asn Gln Lys Thr Glu Trp Pro Glu Leu Val Gly Lys Ser
            20                  25                  30
```

-continued

Val Glu Glu Ala Lys Lys Val Ile Leu Gln Asp Lys Pro Ala Ala Gln
         35                  40                  45

Ile Ile Val Leu Pro Val Gly Thr Ile Val Thr Met Glu Tyr Arg Ile
     50                  55                  60

Asp Arg Val Arg Leu Phe Val Asp Arg Leu Asp Asn Ile Ala Gln Val
 65                  70                  75                  80

Pro Arg Val Gly

<210> SEQ ID NO 27
<211> LENGTH: 4
<212> TYPE: PRT
<213> ORGANISM: Artificial Sequence
<220> FEATURE:
<223> OTHER INFORMATION: Thrombin Inhibitor

<400> SEQUENCE: 27

Ile Gln Pro Arg
1

<210> SEQ ID NO 28
<211> LENGTH: 6
<212> TYPE: PRT
<213> ORGANISM: Artificial Sequence
<220> FEATURE:
<223> OTHER INFORMATION: Thrombin Inhibitor

<400> SEQUENCE: 28

Gly Ser Ala Val Pro Arg
1               5

<210> SEQ ID NO 29
<211> LENGTH: 54
<212> TYPE: PRT
<213> ORGANISM: Artificial Sequence
<220> FEATURE:
<223> OTHER INFORMATION: Furin Activated Furin Inhibitor
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid

<400> SEQUENCE: 29

Thr Lys Lys Val Ala Lys Arg Pro Arg Ala Lys Arg Ala Ala Arg Xaa
1               5                   10                  15

Lys Arg Ser Xaa Thr Lys Lys Val Ala Lys Arg Pro Arg Ala Lys Arg
             20                  25                  30

Ala Ala Arg Xaa Lys Arg Ser Xaa Thr Lys Lys Val Ala Lys Arg Pro
         35                  40                  45

Arg Ala Lys Arg Ala Ala
         50

<210> SEQ ID NO 30
<211> LENGTH: 6
<212> TYPE: PRT

```
<213> ORGANISM: Artificial Sequence
<220> FEATURE:
<223> OTHER INFORMATION: Factor Xa

<400> SEQUENCE: 30

Ile Glu Gly Arg Ser Val
1               5

<210> SEQ ID NO 31
<211> LENGTH: 6
<212> TYPE: PRT
<213> ORGANISM: Artificial Sequence
<220> FEATURE:
<223> OTHER INFORMATION: Furin
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 31

Arg Xaa Lys Arg Ser Xaa
1               5

<210> SEQ ID NO 32
<211> LENGTH: 6
<212> TYPE: PRT
<213> ORGANISM: Artificial Sequence
<220> FEATURE:
<223> OTHER INFORMATION: Plasminogen activator
<220> FEATURE:
<221> NAME/KEY: misc_feature
<222> LOCATION: (1)..(2)
<223> OTHER INFORMATION: Xaa can be any naturally occurring amino acid

<400> SEQUENCE: 32

Xaa Xaa Arg Arg Ile Asn
1               5

<210> SEQ ID NO 33
<211> LENGTH: 6
<212> TYPE: PRT
<213> ORGANISM: Artificial Sequence
<220> FEATURE:
<223> OTHER INFORMATION: Urokinase
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 33

Xaa Ser Gly Arg Xaa Arg
1               5

<210> SEQ ID NO 34
<211> LENGTH: 7
<212> TYPE: PRT
<213> ORGANISM: Artificial Sequence
<220> FEATURE:
<223> OTHER INFORMATION: MMP1
<220> FEATURE:
<221> NAME/KEY: misc_feature
<222> LOCATION: (3)..(3)
<223> OTHER INFORMATION: Xaa can be any naturally occurring amino acid
```

```
<220> FEATURE:
<221> NAME/KEY: misc_feature
<222> LOCATION: (6)..(6)
<223> OTHER INFORMATION: Xaa can be any naturally occurring amino acid

<400> SEQUENCE: 34

Gly Pro Xaa Gly Leu Xaa Gly
1               5

<210> SEQ ID NO 35
<211> LENGTH: 7
<212> TYPE: PRT
<213> ORGANISM: Artificial Sequence
<220> FEATURE:
<223> OTHER INFORMATION: MMP8

<400> SEQUENCE: 35

Gly Pro Gln Gly Leu Arg Gly
1               5

<210> SEQ ID NO 36
<211> LENGTH: 7
<212> TYPE: PRT
<213> ORGANISM: Artificial Sequence
<220> FEATURE:
<223> OTHER INFORMATION: MMP 13
<220> FEATURE:
<221> NAME/KEY: misc_feature
<222> LOCATION: (6)..(6)
<223> OTHER INFORMATION: Xaa can be any naturally occurring amino acid

<400> SEQUENCE: 36

Gly Pro Pro Gly Leu Xaa Gly
1               5

<210> SEQ ID NO 37
<211> LENGTH: 8
<212> TYPE: PRT
<213> ORGANISM: Artificial Sequence
<220> FEATURE:
<223> OTHER INFORMATION: Membrane matrix metalloprotease 1
<220> FEATURE:
<221> NAME/KEY: misc_feature
<222> LOCATION: (8)..(8)
<223> OTHER INFORMATION: Xaa can be any naturally occurring amino acid

<400> SEQUENCE: 37

Leu Pro Ala Gly Leu Val Leu Xaa
1               5

<210> SEQ ID NO 38
<211> LENGTH: 7
<212> TYPE: PRT
<213> ORGANISM: Artificial Sequence
<220> FEATURE:
<223> OTHER INFORMATION: PSA

<400> SEQUENCE: 38

Ser Ser Gln Tyr Ser Ser Asn
1               5

<210> SEQ ID NO 39
<211> LENGTH: 8
<212> TYPE: PRT
<213> ORGANISM: Artificial Sequence
<220> FEATURE:
<223> OTHER INFORMATION: Kallikrein 2

<400> SEQUENCE: 39
```

```
Gly Gly Leu Arg Ser Gly Gly Gly
1               5

<210> SEQ ID NO 40
<211> LENGTH: 7
<212> TYPE: PRT
<213> ORGANISM: Artificial Sequence
<220> FEATURE:
<223> OTHER INFORMATION: Granzyme A
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 40

Thr Xaa Xaa Pro Arg Ser Xaa
1               5

<210> SEQ ID NO 41
<211> LENGTH: 6
<212> TYPE: PRT
<213> ORGANISM: Artificial Sequence
<220> FEATURE:
<223> OTHER INFORMATION: Granzyme B
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 41

Val Glu Xaa Asp Ser Xaa
1               5

<210> SEQ ID NO 42
<211> LENGTH: 5
<212> TYPE: PRT
<213> ORGANISM: Artificial Sequence
<220> FEATURE:
<223> OTHER INFORMATION: Granzyme M
<220> FEATURE:
<221> NAME/KEY: misc_feature
<222> LOCATION: (5)..(5)
<223> OTHER INFORMATION: Xaa can be any naturally occurring amino acid

<400> SEQUENCE: 42

Lys Val Pro Leu Xaa
1               5

<210> SEQ ID NO 43
<211> LENGTH: 7
<212> TYPE: PRT
<213> ORGANISM: Artificial Sequence
<220> FEATURE:
<223> OTHER INFORMATION: Cathespin B
<220> FEATURE:
```

```
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 43

Xaa Leu Arg Xaa Xaa Gly Gly
1               5

<210> SEQ ID NO 44
<211> LENGTH: 7
<212> TYPE: PRT
<213> ORGANISM: Artificial Sequence
<220> FEATURE:
<223> OTHER INFORMATION: Cathespin S
<220> FEATURE:
<221> NAME/KEY: misc_feature
<222> LOCATION: (6)..(6)
<223> OTHER INFORMATION: Xaa can be any naturally occurring amino acid

<400> SEQUENCE: 44

Ser Gly Phe Arg Ser Xaa Gly
1               5

<210> SEQ ID NO 45
<211> LENGTH: 7
<212> TYPE: PRT
<213> ORGANISM: Artificial Sequence
<220> FEATURE:
<223> OTHER INFORMATION: Thrombin
<220> FEATURE:
<221> NAME/KEY: misc_feature
<222> LOCATION: (7)..(7)
<223> OTHER INFORMATION: Xaa can be any naturally occurring amino acid

<400> SEQUENCE: 45

Ala Gly Pro Arg Ser Leu Xaa
1               5

<210> SEQ ID NO 46
<211> LENGTH: 6
<212> TYPE: PRT
<213> ORGANISM: Artificial Sequence
<220> FEATURE:
<223> OTHER INFORMATION: Plasmin
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 46

Ala Xaa Leu Lys Ser Xaa
1               5

<210> SEQ ID NO 47
<211> LENGTH: 6
<212> TYPE: PRT
<213> ORGANISM: Artificial Sequence
<220> FEATURE:
<223> OTHER INFORMATION: Plasminogen
<220> FEATURE:
<221> NAME/KEY: misc_feature
<222> LOCATION: (2)..(2)
<223> OTHER INFORMATION: Xaa can be any naturally occurring amino acid
```

-continued

```
<220> FEATURE:
<221> NAME/KEY: misc_feature
<222> LOCATION: (6)..(6)
<223> OTHER INFORMATION: Xaa can be any naturally occurring amino acid

<400> SEQUENCE: 47

Ala Xaa Leu Lys Ser Xaa
1               5
```